United States Patent [19]

Tennant

[11] Patent Number: 4,960,418
[45] Date of Patent: Oct. 2, 1990

[54] SURGICAL INSTRUMENT AND METHOD FOR CUTTING THE LENS OF AN EYE

[76] Inventor: Jerald L. Tennant, 806 Greentree Ct., Duncanville, Tex. 75137

[21] Appl. No.: 341,140

[22] Filed: Apr. 20, 1989

[51] Int. Cl.$^5$ .................... A61B 17/32; A61B 17/28
[52] U.S. Cl. ................................ 606/107; 606/206; 606/162
[58] Field of Search ................ 606/205–210, 606/107, 138, 167, 170, 171, 162; 30/116, 188, 191

[56] References Cited

U.S. PATENT DOCUMENTS

| | | | |
|---|---|---|---|
| 3,882,872 | 5/1975 | Douvas et al. | 606/107 |
| 4,047,532 | 9/1977 | Phillips et al. | 606/107 |
| 4,198,980 | 4/1980 | Clark | 606/107 |
| 4,325,375 | 4/1982 | Nevyas | 606/207 |
| 4,516,458 | 5/1985 | Pomerantz et al. | 30/16 |
| 4,732,150 | 3/1988 | Keener, Jr. | 606/107 |
| 4,844,065 | 7/1989 | Faulkner | 606/107 |

Primary Examiner—Robert A. Hafer
Assistant Examiner—Kerry Owens
Attorney, Agent, or Firm—Ross, Howison, Clapp & Korn

[57] ABSTRACT

An ophthalmic surgical instrument (10) for cutting the lens (76) of an eye (70) includes first (12) and second (14) handle members which are interconnected for movement between an open position and a closed position. A wire loop (20) extends from the first end (12a) of the first handle member (12). A plate member (22) is interconnected to the first end (14a) of the second handle member (14) and is disposed adjacent the wire loop (20). In the open position of the handle members (12, 14), the wire loop (20) is spaced apart from the plate member (22) to receive the lens (76) therebetween. In the closed position of the handle members (12, 14), the wire loop (20) contacts the plate member (22) to cut the lens (76) disposed therebetween as the wire loop (20) presses the lens (76) against the plate member (22) to thereby cut the lens (76).

19 Claims, 2 Drawing Sheets

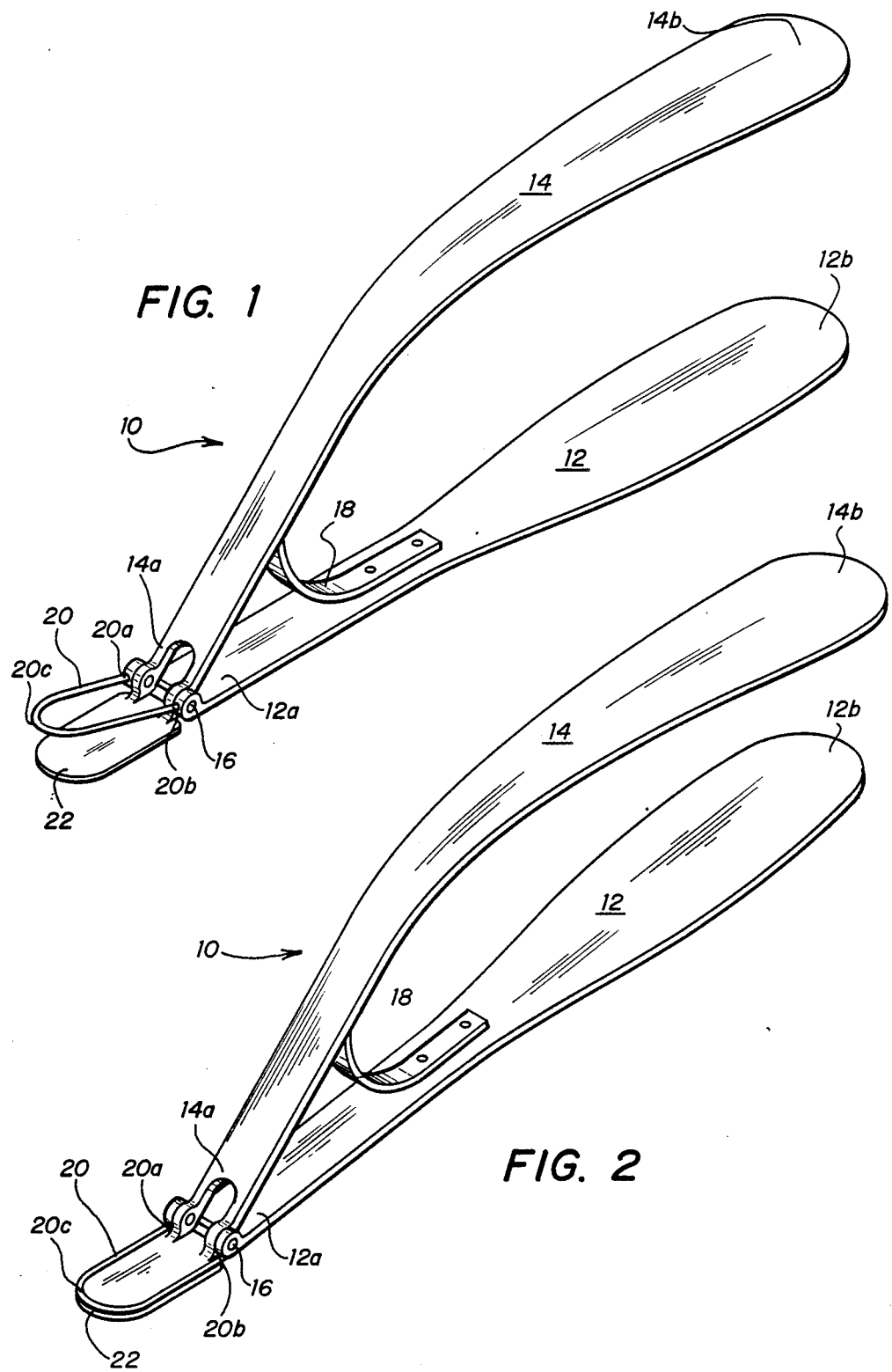

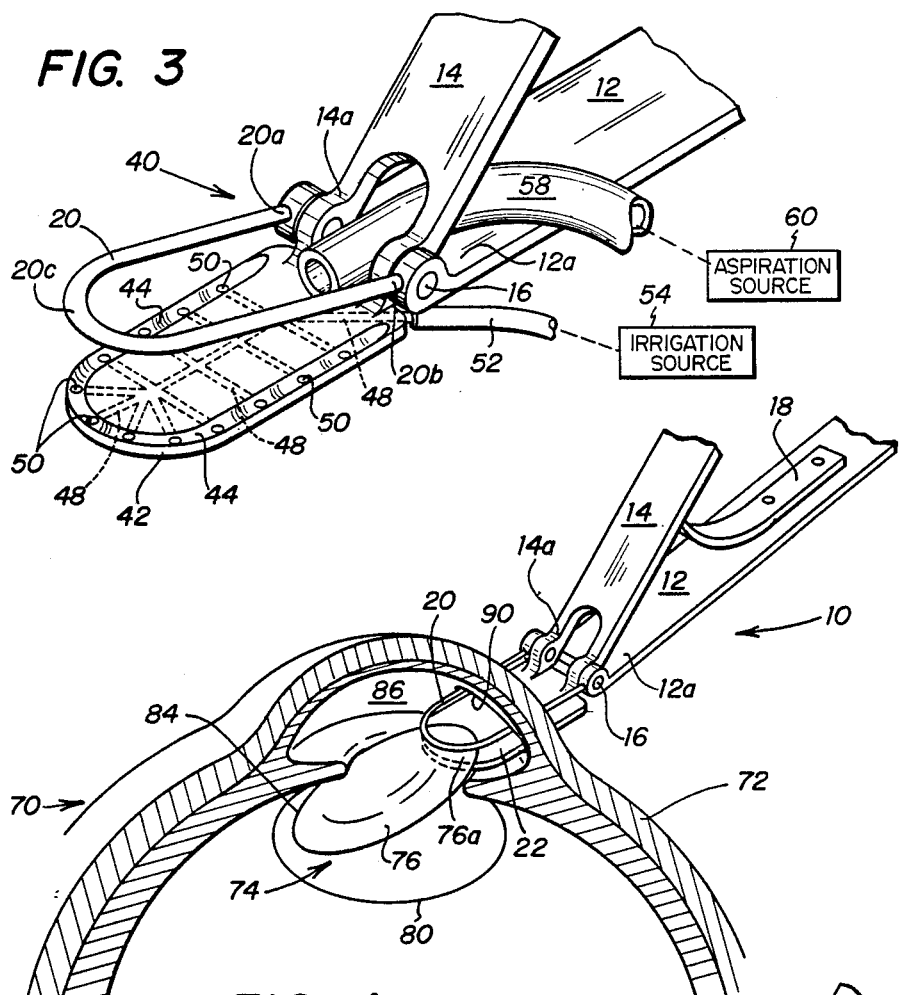
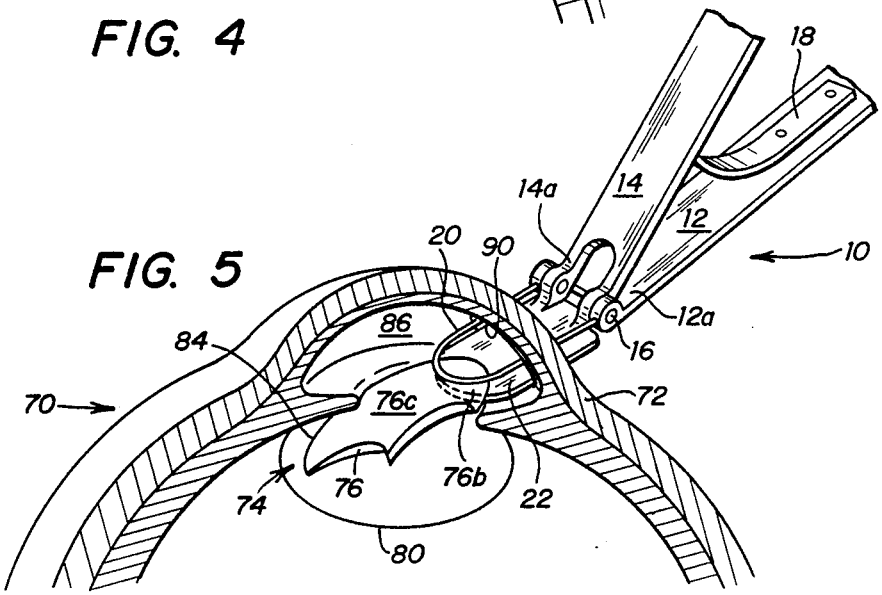

SURGICAL INSTRUMENT AND METHOD FOR CUTTING THE LENS OF AN EYE

TECHNICAL FIELD

This invention relates to surgical instruments, and more particularly to an ophthalmic surgical instrument for cutting the nucleus of the lens of an eye within the eye.

BACKGROUND OF THE INVENTION

The natural lens of an eye is a lenticular-shaped body having three portions. The core portion is the nucleus which is surrounded by a cortex. Enclosing the cortex and constituting the wall of the lens is the capsule. The degenerating or degenerated lens of an eye, or a localized point of degeneration within a lens is referred to as a cataract. As a result of a cataractous degeneration, the lens becomes opaque resulting in visual disability.

Numerous surgical procedures have been developed for removal of cataracted lenses including intracapsular extraction and extracapsular extraction. When the cataract is removed without breaking the capsule, such that the lens is entirely removed, an intracapsular extraction is performed. By contrast, when the forward facing, anterior portion of the capsule is removed followed by separate removal of the lens contents, an extracapsular extraction is performed. Generally, in an extracapsular extraction, the posterior portion of the lens capsule remains in the eye.

In extracapsular cataract extraction, an incision is made into the eye, and the anterior capsule is removed. The size of the nucleus dictates the size of the incision which must be made for the cataract to be extracted. Since the nucleus may be large in diameter for example, approximately 10 millimeters, an incision of 10.5 millimeters to 12 millimeters is employed with this technique. However, a smaller incision would present advantages with respect to reducing operative time, increasing post-operative wound strength, quickening healing and reducing the frequency of bleeding and infection complications. Therefore, techniques have been developed to minimize the diameter of the incision made into the eye for cataract removal. One such technique and instrument developed is described and claimed in U.S. Pat. No. 4,538,611, issued to Charles Kelman on Sept. 3, 1985 and entitled "Surgical Instrument and Method of Cutting a Lens of An Eye". An additional process is described in U.S. Pat. No. 4,732,150, issued to Gerald Keener, Jr. on March 22, 1988 and entitled "Process for Cataract Extraction". In both these methods, a small incision is made into the eye and an instrument is inserted therethrough for cutting the lens into multiple sections so that smaller sections of the lens can be removed through the incision rather than the entire lens. The lens nucleus is moved into the anterior chamber of the eye and is cut into multiple sections prior to removing the individual sections through the incision. Such procedures and instruments; however, require that the entire lens be moved to the anterior chamber of the eye so that the lens can be snared. The lens and the multiple sections cut from the lens may contact the corneal endothelium of the eye resulting in damage to this tissue.

A need has thus arisen for an ophthalmic surgical instrument and method for removing a lens of an eye which minimizes any damage to the endothelium layer of the eye. In such a procedure, containment of the lens and cut portions of the lens must be accomplished prior to removal through the incision made in the eye.

SUMMARY OF THE INVENTION

In accordance with the present invention, an ophthalmic surgical instrument is provided for cutting the lens of an eye. The surgical instrument includes first and second handle members which are interconnected for movement between an open position and a closed position. A wire loop extends from the first end of the first handle member. A plate member is interconnected to the first end of the second handle member and is disposed adjacent the wire loop. In the open position of the handle members, the wire loop is spaced apart from the plate member to receive the lens therebetween. In the closed position of the handle members, the wire loop contacts the plate member to thereby cut the lens disposed therebetween as the wire loop presses the lens against the plate member to thereby cut the lens.

In accordance with another aspect of the present invention, a method for cutting a lens of an eye is provided. The method includes forming an incision in the eye, and freeing the lens from the lens cortical and posterior attachments. A surgical instrument is then inserted into the anterior chamber of the eye. The surgical instrument includes a wire loop extending from a first handle member and a plate member extending from a second handle member, such that the lens portion is disposed between the wire loop and the plate member. The handle members are closed such that the wire loop presses the lens portion against the plate member to cut a semicircular portion of the periphery of the lens. The cut portion of the lens is removed through the incision. The lens in the eye is then allowed to drop back into the posterior chamber and is rotated so that an uncut portion of the lens lies adjacent the incision. The instrument is then inserted into the anterior chamber of the eye and an additional lens portion is cut by closing the handle members of the surgical instrument. The method is continued until the entire periphery of the lens has been cut. A snare is then inserted into the anterior chamber of the eye to remove the remaining central portion of the lens.

BRIEF DESCRIPTION OF DRAWINGS

For a more complete understanding of the present invention and for further advantages thereof, reference is now made to the following Description of the Preferred Embodiments taken in conjunction with the accompanying Drawings in which:

FIG. 1 is a perspective view of the present surgical instrument in the open, non-cutting position;

FIG. 2 is a perspective view of the present surgical instrument in the closed cutting position;

FIG. 3 is a perspective view of an additional embodiment of the present surgical instrument in the open non-cutting position;

FIG. 4 is a cross-sectional view of an eye illustrating the present surgical instrument for cutting of a first periphery portion of the lens; and FIG. 5 is a cross-sectional view of an eye illustrating the present surgical instrument for cutting a second peripheral portion of the lens of the eye after the lens has been rotated.

DESCRIPTION OF THE PREFERRED EMBODIMENTS

Referring simultaneously to FIGS. 1 and 2, the present surgical instrument is illustrated and is generally identified by the numeral 10. Surgical instrument 10 includes a first handle member 12 having ends 12a and 12b. Surgical instrument 10 further includes a second handle member 14 having ends 14a and 14b. Ends 12a and 14a of handle members 12 and 14, respectively, are hingedly interconnected utilizing a hinge 16. Handle members 12 and 14 are adapted to be supported in the hand of a surgeon for use in the surgical procedure of removing a lens of the eye in accordance with the present invention. Surgical instrument 10 may have an overall length of, for example, 10–15 centimeters.

Interconnected between handle members 12 and 14 is a spring 18 for normally biasing handles 12 and 14 spaced apart in an open position as illustrated in FIG. 1. In use, the force exerted by spring 18 is overcome such that ends 12b and 14b of handle members 12 and 14, respectively, are brought together to a closed position illustrated in FIG. 2.

Interconnected to end 12a of handle member 12 is a wire loop, generally identified by the numeral 20. Wire loop 20 has a generally rectangular configuration having ends 20a and 20b which are interconnected to end 12a of handle member 12. Wire loop 20 further includes a curvilinear portion 20c oppositely disposed end 12a of handle member 12. Wire loop 20 may have, for example, a length of 6 millimeters, a width of 3 millimeters and may be composed of, for example, stainless steel wire having a diameter of 0.008–0.015 inches.

Interconnected to end 14a of handle member 14 is a plate 22 which is positioned adjacent to wire loop 20. In operation of the present surgical instrument 10, a portion of a lens is disposed between wire loop 20 and plate 22 in the open position of surgical instrument 10 as illustrated in FIG. 1. Upon compression of spring 18 such that handle members 12 and 14 move towards one another, wire loop 20 engages plate 22 such that the lens is thereby cut. Handle members 12 and 14 are then released to the open position by the action of spring 18 in order to cut additional peripheral portions of the lens to be removed from the eye, as will subsequently be described with respect to FIGS. 4 and 5.

FIG. 3 illustrates a further embodiment of the present surgical instrument, generally identified by the numeral 40. Like numerals are utilized for like and corresponding components previously identified with respect to FIGS. 1 and 2. Surgical instrument 40 includes a plate 42 which includes a groove 44 into which wire loop 20 is received when surgical instrument 40 is in the closed position. The positioning of wire loop 20 within groove 44 insures that the lens will be cut as wire loop 20 will pass through the entire thickness of the lens. Plate 42 further includes an interior chamber 48 which includes a plurality of apertures 50. Interior chamber 48 is interconnected via a flexible tube 52 to an irrigation source 54. Irrigation source 54 may comprise any standard device for providing an irrigating fluid to a surgical site, such devices being well-known to those skilled in the art. Alternatively, Chamber 48 may be a curvilinear type with irrigation ports. The irrigation fluid may include saline or balanced salt solution. Surgical instrument 40 further includes a flexible tube 58 disposed adjacent to plate 42. Flexible tube 58 is interconnected to an aspiration source 60 for aspirating lens fragments from the eye.

Referring now simultaneously to FIGS. 4 and 5, the present method of utilizing the present surgical instrument 10 for cutting the lens of an eye will be described. FIGS. 4 and 5 illustrate an eye generally identified by the numeral 70. Eye 70 includes cornea 72 and a lens generally identified by the numeral 74. Lens 74 includes a nucleus 76 within a capsule 80. Lens 74 is generally disposed within the posterior chamber 84 of eye 70, but is illustrated in FIG. 4 with a portion of nucleus 76 positioned within anterior chamber 86.

An incision 90 is made through cornea 72 into anterior chamber 86 of eye 70. Surgical instruments to make incision 90 are well-known to those skilled in the art, as well as the procedure for making these incisions. The anterior capsule 80 is then opened, and nucleus 76 is freed from its cortical attachments by irrigation under the capsule 80 with a saline solution. Anterior chamber 86 may be filled with a viscoelastic or similar substance if desired. By pressing on incision 90, anterior chamber 86 will begin to collapse to cause the upper portion 76a of nucleus 76 to come forward. An irrigating needle may be placed under portion 76a of nucleus 76 and irrigation may be used to break the posterior attachments of the cortex to the posterior aspect of nucleus 76. This irrigation refills posterior chamber 84 leaving portion 76a of nucleus 76 at the iris plane. Alternatively, a simple incision into the capsule allowing access to the pole of nucleus 76 may be utilized, to cut the nucleus 76 inside the capsule.

Surgical instrument 10 is then inserted through incision 90 and portion 76a of nucleus 76 is cut by closure of handle members 12 and 14, such that wire loop 20 contacts plate 22 thereby cutting nucleus portion 76a of nucleus 76 along the periphery of nucleus 76. Nucleus portion 76a is then removed from anterior chamber 86 along with surgical instrument 10.

Nucleus 76 is then allowed to drop back into posterior chamber 84 and is rotated utilizing a standard surgical probe. Surgical instrument 10 is then reinserted through incision 90 in order to cut an additional portion 76b of nucleus 76. Nucleus 76 is repeatedly rotated and cut such that the entire periphery of nucleus 76 has been removed and only a central portion 76c of nucleus 76 remains within eye 70. A nucleus snare type instrument can then be inserted into eye 70, placed around nucleus portion 70c for removal through incision 90. The nucleus snare may be used to remove central portion 76c of nucleus 76 intact or may be utilized to cut nucleus portion 76a into halves or smaller pieces for removal. Such nucleus snare instruments are well-known to those skilled in the art, such as, for example, the devices shown in U.S. Pat. No. 4,732,150 and U.S. Pat. No. 4,538,611.

Any remaining fragments of nucleus 76 suspended in the viscoelastic substance may be removed from eye 70 with irrigation of the viscoelastic substance utilizing the irrigation source 54 or aspirated utilizing aspiration source 60 (FIG. 3).

It therefore can be seen that the present surgical instrument provides for the cutting of the nucleus of a lens of an eye by removing the periphery of the nucleus so that the entire nucleus can be removed through a 3–4 millimeter incision. Although the present invention has been illustrated as being purely mechanical, handle members 12 and 14 may be operated automatically through a foot-driven machine.

Whereas the present invention has been described with respect to specific embodiments thereof, it will be understood that various changes and modifications will be suggested to one skilled in the art and it is intended to encompass such changes and modifications as fall within the scope of the appended claims.

I claim:

1. A ophthalmic surgical instrument for cutting the lens of an eye comprising:
    a first support member having first and second ends;
    a second support member having first and second ends;
    said support members being interconnected for movement between an open position and a closed position;
    a wire loop extending from said first end of said first support member; and
    a plate member interconnected to said first end of said second support member and being disposed adjacent to said wire loop, such that in said open -position of said support members, said wire loop is spaced apart from said plate member to receive the lens therebetween and in the closed position of said support members, said wire loop contacts said plate member to cut the lens disposed between said wire loop and said plate member by pressing the lens against said plate member and cutting the lens with said wire loop.

2. The surgical instrument of claim 1 wherein said support members are adapted for support in a hand of a user.

3. The surgical instrument of claim 1 and further including:
    means for biasing said support members in the open position.

4. The surgical instrument of claim 1 wherein said support members first ends are hingedly attached and said support members second ends are spaced apart.

5. The surgical instrument of claim 1 wherein said plate member includes a recessed groove for receiving said wire loop in the closed position of said support members.

6. The surgical instrument of claim 1 wherein said plate member further includes:
    a channel having a plurality of apertures; and
    an irrigation source connected to said plate member channel for dispensing irrigating fluid to the eye through said plurality of apertures from said irrigating source.

7. The surgical instrument of claim 1 wherein said wire loop is shaped to form an arcuate cut in the lens periphery.

8. The surgical instrument of claim 1 and further including:
    means interconnected to said plate member for aspirating cut portions of the lens.

9. An ophthalmic surgical instrument for cutting the lens of an eye comprising:
    a first handle member having first and second ends;
    a second handle member having first and second ends;
    said handle members being adapted for support in a hand of a user wherein said first ends of said handle members are hingedly attached and said second ends of said handle members are spaced apart for movement between an open position and a closed position;
    a wire having first and second ends, said wire ends interconnected to said first end of said first handle member to form a loop; and
    a plate member interconnected to said first end of said second handle member, said plate member including a groove for receiving said wire loop, and being disposed to mate with said wire loop when said handle members are in said closed position to cut the lens disposed between said wire loop and said plate member by pressing the lens against said plate member to thereby cut a semicircular portion of the periphery of the lens with said wire loop, said wire loop being spaced apart from said plate member in said open position of said handle members to thereby receive the lens between said wire loop and said plate member.

10. The surgical instrument of claim 9 and further including:
    an irrigation source connected to said plate member for dispensing irrigating fluid to the eye.

11. The surgical instrument of claim 10 and further including:
    means interconnected to said plate member for aspirating cut portions of the lens from the eye.

12. The surgical instrument of claim 9 and further including:
    means for biasing said handle members in said open position.

13. The surgical instrument of claim 12 wherein said biasing means includes a spring extending between said handle members.

14. A method for cutting a lens of an eye comprising the steps of:
    forming an incision in the eye; posterior attachments; gaining access to the lens;
    inserting into the anterior chamber of the eye a surgical instrument having a wire loop extending from a first handle member and a plate member extending from a second handle member such that the lens portion is disposed between the wire loop and the plate member;
    closing the handle members such that the wire loop presses the lens portion against the plate member to thereby cut a semicircular portion of the periphery of the lens; and
    removing the cut portion of the lens through the incision.

15. The method of claim 14 and further including:
    allowing the lens to drop back into the posterior chamber of the eye;
    rotating the lens so that an uncut portion of the lens periphery lies adjacent to the incision;
    cutting an additional lens portion utilizing the surgical instrument by closing the handle members of the surgical instrument to remove an additional semicircular portion of the periphery of the lens.

16. The method of claim 15 and further including:
    repeatedly rotating and cutting additional portions of the lens periphery until the entire periphery of the lens has been cut; and
    inserting a snare instrument into the eye to remove the remaining central portion of the lens.

17. The method of claim 16 and further including:
    cutting the central portion of the lens with the snare instrument and removing the cut portion through the incision.

18. The method of claim 14 and further including the step of irrigating the eye by providing an irrigation fluid from a source through the plate member.

19. The method of claim 14 and further including the step of:
    aspirating the eye by providing an aspiration source adjacent to the plate member.

* * * * *